(12) United States Patent
Han et al.

(10) Patent No.: US 7,304,096 B2
(45) Date of Patent: *Dec. 4, 2007

(54) HIGHLY FUNCTIONAL DENTAL ADHESIVE COMPOSITION

(75) Inventors: Dong Keun Han, Seoul (KR); Kyu Hyun Baek, Goyang-si (KR); Min Sung Kim, Gunpo-si (KR); Sang Soon Park, Seoul (KR); Hyun Chul Goo, Seoul (KR); Choong Ho Kim, Hwaseong-si (KR)

(73) Assignee: Korea Institute of Science and Technology and Dentkist, Inc. (KR)

( * ) Notice: Subject to any disclaimer, the term of this patent is extended or adjusted under 35 U.S.C. 154(b) by 314 days.

This patent is subject to a terminal disclaimer.

(21) Appl. No.: 11/025,337

(22) Filed: Dec. 29, 2004

(65) Prior Publication Data

US 2005/0277706 A1    Dec. 15, 2005

(30) Foreign Application Priority Data

Jun. 9, 2004   (KR) .................. 10-2004-0042043

(51) Int. Cl.
C08F 2/46 (2006.01)
C08F 2/50 (2006.01)
A61K 6/083 (2006.01)

(52) U.S. Cl. .................. 522/100; 522/77; 522/83; 522/81; 522/79; 522/109; 522/111; 522/170; 522/181; 522/908; 522/182; 523/115; 523/116; 523/113; 523/111; 523/117; 523/118; 433/288.1; 433/180

(58) Field of Classification Search ........... 523/109, 523/116, 117, 118, 115, 113, 111; 522/84, 522/86, 85, 79, 181, 182, 183, 103; 433/228.1, 433/180; 22/100, 77, 79, 83, 109, 111, 170, 22/182, 181, 908
See application file for complete search history.

(56) References Cited

U.S. PATENT DOCUMENTS 3,066,112 A * 11/1962 Bowen .................. 523/116
3,730,947 A * 5/1973 Stoffey et al. ............ 526/313
4,102,856 A * 7/1978 Lee, Jr. .................... 523/116
4,131,729 A * 12/1978 Schmitt et al. ............ 526/282
4,381,918 A * 5/1983 Ehrnford .................. 523/115
4,491,453 A * 1/1985 Koblitz et al. ............ 523/116
4,540,723 A * 9/1985 Ying ........................ 523/115
4,544,467 A * 10/1985 Bunker et al. .............. 522/13
4,669,983 A * 6/1987 Bunker .................. 433/217.1
4,674,980 A * 6/1987 Ibsen et al. ............ 433/228.1
4,966,934 A * 10/1990 Huang et al. .............. 524/315
5,177,121 A * 1/1993 Bunker .................... 523/116
5,334,625 A * 8/1994 Ibsen et al. ................ 523/115
5,766,559 A * 6/1998 Blanchet et al. ........... 422/171
6,184,339 B1 * 2/2001 Stansbury et al. .......... 528/407
6,339,113 B1 * 1/2002 Han et al. .................. 522/100
6,573,312 B2 * 6/2003 Han et al. .................. 523/116
2004/0176496 A1 * 9/2004 Han et al. .................. 522/183

* cited by examiner

Primary Examiner—Sanza L. McClendon
(74) Attorney, Agent, or Firm—Jones Day

(57) ABSTRACT

There is provided a highly functional one-step light-curing dental adhesive composition i) based on a multifunctional prepolymer mixture of 2,2-bis-[4-(2-hydroxy-3-methacryloyloxypropoxy)phenyl]propane ("Bis-GMA") and a multifunctional prepolymer formed by substituting hydrogen atoms of hydroxyl groups present in Bis-GMA molecules with methacrylate groups, in which the Bis-GMA is used as a base prepolymer of conventional dental adhesive compositions; and ii) comprising and acidic monomer for removing a portion of smear layer, which is allowed to be bonded without separate treatment of acid etchant, an adhesive monomer having both hydrophobic and hydrophilic properties, a hydrophilic monomer which is allowed to be bonded in the present of moisture, an inorganic filler for improving mechanical properties, diluent, water for demineralization, a photoinitiation system and other additives.

11 Claims, No Drawings

HIGHLY FUNCTIONAL DENTAL ADHESIVE COMPOSITION

FIELD OF THE INVENTION

The present invention relates to a highly functional one-step light-curing dental adhesive composition that is applied to the mouth and that can simultaneously perform the treatments of an acid etchant, a primer and adhesive agent. The composition not only has more enhanced mechanical and physical properties than any adhesive composition which separately applies an acid etchant, a primer and an adhesive agent, but also keeps such properties for a long period of time after its application.

More specifically, the present invention relates to a new one-step light-curing dental adhesive composition: i) based on a multifunctional prepolymer mixture of 2,2-bis-[4-(2-hydroxy-3-methacryloyloxypropoxy)phenyl]propane ("Bis-GMA") and a multifunctional prepolymer formed by substituting hydrogen atoms of hydroxyl groups presented in Bis-GMA molecules with methacrylate groups, in which the Bis-GMA is used as a base prepolymer of a conventional dental adhesive composition; and ii) comprising an acidic monomer for removing a portion of smear layer, which is allowed to be bonded without separate treatment of acid etchant, an adhesive monomer having both hydrophobic and hydrophilic properties, a hydrophilic monomer that is allowed to be bonded in the presence of moisture, an inorganic filler for improving mechanical properties, diluent, water for demineralization, a photoinitiation system and other additives. The performance of the composition mainly depends on an acidic monomer, an adhesive monomer, an inorganic filler, diluent, water, and a photoinitiation system constituting the composition.

BACKGROUND OF THE INVENTION

Generally, dental adhesion is divided into enamel adhesion and dentine adhesion. In case of enamel adhesion, it was found in 1995 by Buonocore that sustainability could be enhanced through changing a soft surface of enamel to a rough surface via acid corrosion in order to facilitate capillary phenomenon development therein. This allows a dental restoration material to permeate through minute pores. As such, excellent physical properties could be achieved via enamel adhesion (see U.S. Pat. Nos. 4,102,856 and 4,131,729, etc).

Furthermore, in case of dentine adhesion, enamel is considered non-live tissue while dentine is considered as being an extension of the dental pulp. Therefore, any materials that are applied to dentine should not have any biologically detrimental effects or threaten the biological stability of the teeth.

Kanca demonstrated that if a primer having high hydrophilic property and an adhesive monomer having both hydrophilic and hydrophobic properties are used together, the bonding strength becomes stronger (see Japanese Laid Open Patent Publication Nos. 53-33687 and 54-10986, and Japanese Patent Application No. 56-120610). Thereafter, various compounds have been suggested, and the treating method has been further developed. Recently, products that exhibit excellent bonding strength were mainly used. These products were applied in a two-step procedure, first involving treatment with an acid etchant and a primer, an adhesive agent or an acid etchant, and then with a primer and an adhesive agent.

Also, in case of dentine adhesion, an acid etchant, a primer and an adhesive agent is applied in a one-step procedure. However, there is a problem in that the bonding strength obtained via the one-step procedure is lower than that obtained by the aforementioned two-step procedure.

SUMMARY OF THE INVENTION

It is an object of the present invention to provide a highly functional one-step light-curing dental adhesive composition capable of being applied in a one-step procedure while improving mechanical and physical properties.

This and other objects and advantages of the invention will be clarified in the following detailed description of the invention provided below.

DETAILED DESCRIPTION OF THE PRESENT INVENTION

As used herein, "one-step" means the system of applying an acid etchant, a primer and an adhesive agent at once.

Generally, Bis-GMA has been most frequently used as a prepolymer for dental adhesive. This is because of its superior physical properties, such as its high strength after curing. Bis-GMA molecule has two hydroxyl groups and two methacrylate groups capable of being polymerized by a light. The hydroxyl groups have a property to absorb moisture, which reduces the physical properties of a photocured substance. Thus, if a polymerized resin becomes swollen by water-absorption, then its binding force within cured resin is weakened so that the particles are likely to separate from the resin. Consequently, the photocured substance is weakened with respect to its physical properties, such as its strength and abrasion resistance so that cytotoxicity may be generated.

The present inventors have conducted an extensive research to solve the aforesaid problems of conventional photocured dental adhesive material prepared solely from Bis-GMA prepolymer. The present inventors have found that a prepolymer mixture of Bis-GMA and trifunctional methacrylate prepolymer (Tri-GMA) and/or tetrafunctional methacrylate prepolymer (Tetra-GMA) that is formed by substituting one or two hydrogen atoms of two hydroxyl groups present in Bis-GMA molecule with methacrylate groups can be used together with a conventional adhesive monomer in preparing a light-curing dental adhesive material. By doing so, improved physical and mechanical properties, and low polymerization shrinkage of photo-cured substance, can be obtained.

Further, the present inventors have found that if an acidic monomer having carboxylic acid or carboxylic anhydride group in the molecule is also used together, the separate treatment of an acid etchant is not necessary. Also, the bonding strength becomes higher.

Therefore, the present invention relates to a highly functional one-step light-curing dental adhesive composition i) comprising a multifunctional prepolymer mixture of Tri-GMA and/or Tetra-GMA with Bis-GMA, an acidic monomer, an adhesive monomer, a hydrophilic monomer, an inorganic filler, diluent, water, a photoinitiation system and other additives, and ii) exhibiting improved physical and mechanical properties, and adhesive performance.

More specifically, the present invention provides a highly functional one-step light-curing dental adhesive composition, which exhibits improved physical and mechanical properties, and adhesive performance, comprising:

(a) 1 to 50 wt % of the prepolymer mixture selected from a group consisting of a mixture of Bis-GMA of formula 1 with Tri-GMA of formula 2, a mixture of Bis-GMA with Tetra-GMA of formula 3 and a mixture of Bis-GMA, Tri-GMA and Tetra-GMA;
(b) 1 to 30 wt % of an acidic monomer;
(c) 1 to 40 wt % of an adhesive monomer;
(d) 1 to 10 wt % of a hydrophilic monomer;
(e) 0.1 to 5 wt % of an inorganic filler;
(f) 10 to 60 wt % of diluent;
(g) water;
(h) a photoinitiation system; and
(i) other additives,
wherein the wt % of all the components are based on the total weight of the composition;

position comprising 1 to 50 wt % of the prepolymer mixture of Bis-GMA of formula 1, Tri-GMA of formula 2 and Tetra-GMA of formula 3, 1 to 30 wt % of an acidic monomer, 1 to 40 wt % of an adhesive monomer, 1 to 10 wt % of a hydrophilic monomer, 0.1 to 5 wt % of an inorganic filler, 10 to 60 wt % of diluent, water, a photoinitiation system and other additives, wherein the wt % of all the components are based on the total weight of the composition. The prepolymer mixture consists of 90 to 5 wt % of Bis-GMA of formula 1, 90 to 5 wt % of Tri-GMA of formula 2, and 90 to 5 wt % of Tetra-GMA of formula 3 on the basis of the total weight of the prepolymer mixture.

In accordance with the present invention, the highly functional one-step light-curing dental adhesive composition comprises a prepolymer mixture in an amount of from

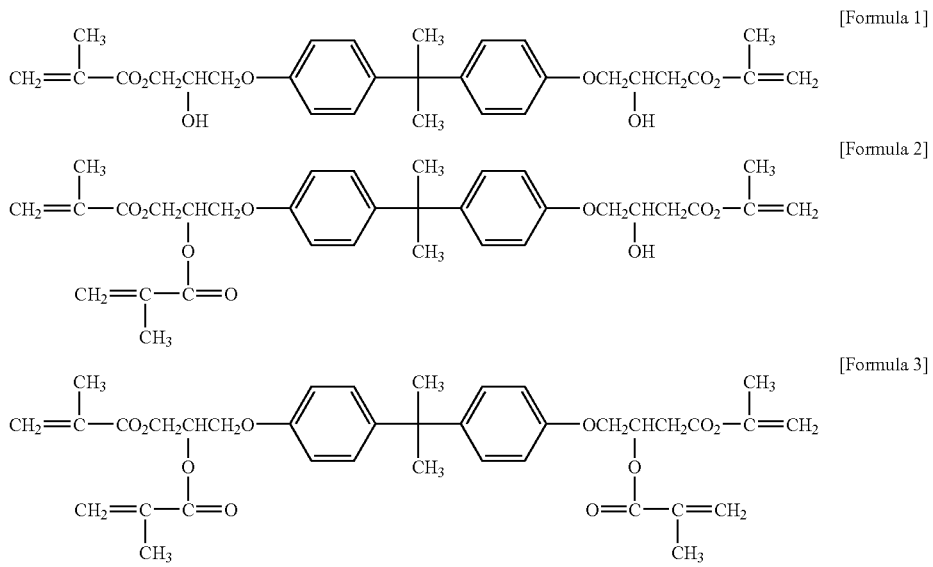

The present invention will now be described in detail.

According to the first embodiment, there is provided a highly functional one-step light-curing dental adhesive composition comprising 1 to 50 wt % of the prepolymer mixture of Bis-GMA of formula 1 and Tri-GMA of formula 2, 1 to 30 wt % of an acidic monomer, 1 to 40 wt % of an adhesive monomer, 1 to 10 wt % of a hydrophilic monomer, 0.1 to 5 wt % of an inorganic filler, 10 to 60 wt % of diluent, water, a photoinitiation system and other additives, wherein the wt % of all the components are based on the total weight of the composition. The weight ratio of Bis-GMA of formula 1 to Tri-GMA of formula 2 is 95:5 to 5:95.

According to the second embodiment, there is provided a highly functional one-step light-curing dental adhesive composition comprising 1 to 50 wt % of the prepolymer mixture of Bis-GMA of formula 1 and Tetra-GMA of formula 3, 1 to 30 wt % of an acidic monomer, 1 to 40 wt % of an adhesive monomer, 1 to 10 wt % of a hydrophilic monomer, 0.1 to 5 wt % of an inorganic filler, 10 to 60 wt % of diluent, water, a photoinitiation system and other additives, wherein the wt % of all the components are based on the total weight of the composition. The weight ratio of Bis-GMA of formula 1 to Tetra-GMA of formula 3 is 95:5 to 5:95.

According to the third embodiment, there is provided a highly functional one-step light-curing dental adhesive com- 1 to 50 wt % of the total weight of the composition. If the amount of used prepolymer mixture is less than 1 wt %, the effect by itself is insufficient. If the amount of used prepolymer mixture is more than 50 wt %, the viscosity of the composition may be too high.

The composition according to the present invention comprises the acidic monomer to provide improved bonding strength to the teeth without having to undergo a separate application of acid etchant. The acidic monomer should contain carboxylic acid or carboxylic anhydride group in the molecule. Preferred examples of the acidic monomer to be used in the present invention include 4-(meth)acryloxymethyltrimellitic acid and its anhydride, 4-(meth)acryloxyethyltrimellitic acid and its anhydride, 4-(meth)acryloxypropyltrimellitic acid and its anhydride, 4-(meth)acryloxybutyltrimellitic acid and its anhydride, 4-(meth)acryloxypentyltrimellitic acid and its anhydride, 4-(meth)acryloxyhexyltrimellitic acid and its anhydride, 4-(meth)acryloxyoctyltrimellitic acid and its anhydride. Among them, 4-methacryloxyethyltrimellitic acid (4-MET) and its anhydride (4-META), 4-methacryloxybutyltrimellitic acid (4-MBT) and its anhydride (4-MBTA), and 4-methacryloxyoctyltrimellitic acid (4-MOT) and anhydride (4-MOTA) are more preferably used. The acidic monomer can be used alone or in any combination thereof, and is suitably used in an amount of from 1 to 30 wt % based on the total weight of the composition. If the acidic monomer is used in an amount of less than 1 wt % based on the total weight of the composition, it is rarely possible to obtain the effect by itself. Also, if the amount of used acidic monomer is more than 30 wt %, histotoxicity may be generated.

In the present composition, the adhesive monomer is formed to improve the adhesive property with the teeth. The adhesive monomer should be a polymerizable monomer having at least one phosphoric acid groups in the molecule. Examples of the polymerizable monomer include 2-(meth)acryloyloxyethyl acid phosphate, 2- and 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis[2-(meth)acryloyloxyethyl]acid phosphate, 2-(meth)acryloyloxyethylphenyl acid phosphate, 2-(meth)acryloyloxyethyl p-methoxyphenyl acid phosphate. Particularly, 2-methacryloyloxyethyl acid phosphate (MEP) and 10-methacryloyloxydecyl acid phosphate (MDP) are preferred. The polymerizable monomer can be used alone or in any combination thereof, and are suitably used in an amount of from 1 to 40 wt % based on the total weight of the composition. If the polymerizable monomer is used in an amount of less than 1 wt % based on the total weight of the composition, then it is rarely possible to obtain the effect by itself. Also, if the amount of used adhesive monomer is more than 40 wt %, then the physical properties may become lower.

In the present composition, the hydrophilic monomer, which is allowed to be bonded in the presence of moisture, is used because the teeth contain a number of moisture. Examples of such a hydrophilic monomer include hydroxyethyl methacrylate (HEMA) and hydroxypropyl methacrylate (HPMA). The hydrophilic monomer is used in an amount of from 1 to 10 wt % based on the total weight of the composition. If the hydrophilic monomer is used in an amount of less than 1 wt %, then it is rarely possible to obtain the effects by itself. Also, if the amount of used hydrophilic monomer is more than 40 wt %, then the composition is too hydrophilic, thereby lowering the physical properties.

In the composition according to the present invention, the inorganic filler is comprised to fill fine structure of smear layer removed by the acidic monomer in order to improve the mechanical properties. Preferred examples of inorganic fillers include quartz, barium glass, barium glass/silica, quartz/barium glass, silica, zirconia/silica, aluminosilicate, lithium aluminosilicate and barium aluminosilicate, etc., having a particle diameter of from 0.0005 to 20 μm, of which surface is treated with silane coupling agent. The inorganic filler is used in an amount of from 0.1 to 5 wt % based on the total weight of the composition.

In accordance with the present invention, the composition comprises a diluent to reduce the viscosity of the composition and to remove water of the teeth by means of its high volatility. The suitable examples of the diluent include ethanol, acetone, etc. The composition comprises the diluent in an amount of from 10 to 60 wt % based on the total weight of the composition.

In order to promote the demineralization after removing a portion of smear layer by the acidic monomer, the present composition comprises water in an amount of from 1 to 10 wt % based on the total weight of the composition.

The dental adhesive composition of the present invention is exposed to visible rays that are unharmful to the human body so as to form a radical from a photoinitiator and a reductant. Said radical initiates polymerization of monomers for curing the composition. Polymerization primarily occurs by exposure of a photoinitiator such as α-diketone aliphatic and aromatic carbonyl compound and tert-amine reductant to the visible ray under a wavelength ranging from 400 to 500 nm. The photoinitiation system as used herein consists of a photoinitiator and a reductant. The photoinitiator is preferably camphorquinone (CQ), and added in an amount of from 0.05 to 5 wt % of the total weight of the composition. If CQ is photoexcited to extract hydrogen from the reductant, the reductant practically initiates radical polymerization. The reductant such as N,N-dimethylaminoethyl methacrylate (DMAEMA) or ethyl p-dimethyl aminobenzoate (EDMAB) is added in an amount of from 0.05 to 5 wt % based on the total weight of the composition.

The present invention is illustrated in detail by the examples provided below. However, the examples presented below are only for illustrative purposes and should not be construed as limiting the present invention.

The physical properties of the dental adhesive compositions prepared in each example are estimated as follows:

1) Photoconversion

Photopolymerization efficiency caused by the visible ray is estimated by means of infrared absorption spectroscopy. The conversion of methacrylate monomer is calculated by measuring the decreased area of the absorption band at 1638 cm-1 by the aliphatic double bond on the basis of the area of the absorption band at 1690 cm-1 by the aromatic ring.

2) Polymerization Shrinkage

A cylindrical specimen of the dental adhesive composition [6.0 cm (diameter)×3.3 mm (height)] is put into a transparent glass mold, and then cured using a light curing unit. A density of the specimen before and after curing is measured using a picnometer.

3) Water Absorption and Solubility

A dental adhesive composition is made into about a 6 cm (diameter)×3 mm (thickness) specimen, which is cured. The weight of the cured specimen is measured, and then the specimen is dipped into distilled water at 37° C. After every 24 or 48 hours, the specimen is then taken out, water is removed from a surface of the specimen, and the weight of the specimen is measured. Water absorption is calculated by the following formula.

$$\text{Water Absorption}(\%) = \frac{\text{weight after dipping} - \text{weight after cure before dipping}}{\text{weight after cure before dipping}} \times 100$$

In order to measure solubility, the specimen is taken out, and water is removed from the specimen. The specimen is dried again in a desiccator until the weight is constant, and the weight is recorded as weight after dipping and complete drying. Solubility is calculated by the following formula.

$$\text{Solubility}(\%) = \frac{\text{weight after cure before dipping} - \text{weight after dipping and complete drying}}{\text{weight after cure before dipping}} \times 100$$

4) Radiopacity

A 13 mm [diameter]×2 mm [thickness] specimen of the composition is prepared and placed on a radioactive film together with aluminum step-panel of 2 mm thickness having a purity of 99.9%. The film is exposed to a radioactive ray (65±5 kvp, 15 mA) for 0.05 sec and developed. The radiopacity of the specimen is determined using a densitometer and comparing with 2 mm aluminum step wedge.

5) Dentine Bonding Strength

Tooth specimen having a uniform thickness is cut in parallel with occlusal surface using a microtome and then a tube containing the composition is attached to the dentine to determine the bonding strength using Instron.

6) Cytotoxicity

An L-29 cell suspension ($3 \times 10^5$/ml) is prepared and poured 10 ml of it into 90 mm petridich. Then, the cell is cultured for 24 hours. After removing enriched solution, 10 ml Eagle's agar medium at 45-50° C. is added to the petridish. The petridish is placed at room temperature for 30 minutes, resulting in solidification of the Eagle's agar medium. 10 ml neutral vivo staining solution is slowly added on the central portion of the medium, and is placed for 30 minutes after spreading through the front surface of the medium. After removing the staining solution, the specimen of the composition is closely placed on the medium as soon as possible. Then, the cell is cultured in 37° C., 5% $CO_2$ incubator for 24 hours. The cell lysis ratio is measured in a discolored region of the specimen and is indicated in a zone index and in Table 1, from which a response index (RI=zone index/lysis index) is calculated. Cytotoxicity is evaluated from RI value as in Table 2. The lower value means a lower toxicity.

TABLE 1

Definition of each index value

| Index | Definition |
| --- | --- |
| Zone Index | |
| 0 | None permeation under the specimen |
| 1 | The limited portion under the specimen |
| 2 | Portion diffused from sample <0.5 cm |
| 3 | Portion diffused from sample <1.0 cm |
| 4 | Portion diffused from sample ≧1.0 cm |
| 5 | Portion diffused from sample: total portion |
| Lysis Index | |
| 0 | None |
| 1 | <20% |
| 2 | 20-40% |
| 3 | 40-60% |
| 4 | 60-80% |
| 5 | ≧80% |

TABLE 2

Evaluation of cytotoxicity

| Scale | Response Index (RI) | Cytotoxicity |
| --- | --- | --- |
| 0 | 0/0 | None |
| 1 | 1/1 | Weak |
| 2 | 2/2 to 3/3 | Medium |
| 3 | 4/4 to 5/5 | Severity |

EXAMPLE 1

The following was mixed to prepare a light-curing dental adhesive composition: 8 wt % of Bis-GMA, 8 wt % of Tri-GMA, 15 wt % of 4-methacryloxybutyltrimellitic anhydride (4-MBTA) as an acidic monomer, 25 wt % of 10-methacryloyloxydecyl acid phosphate (MDP) as an adhesive monomer, 15 wt % of hydroxypropyl methacrylate (HPMA) as a hydrophilic monomer, 2 wt % of barium glass/silica as an inorganic filler, 23 wt % of ethanol as diluent, 2 wt % of water, 1 wt % of camphorquinone (CQ) as a photoinitiator, and 1 wt % of N,N-dimethylaminoethyl methacrylate (DMAEMA) as a reductant. The physical properties of the prepared adhesive composition measured as described above were shown in Table 3 below.

EXAMPLE 2

The following was mixed to prepare a light-curing dental adhesive composition: 25 wt % of a prepolymer mixture consisting of 70 wt % of Bis-GMA and 30 wt % of Tri-GMA, 30 wt % of 4-methacryloxybutyltrimellitic acid (4-MBT) as an acidic monomer, 10 wt % of 2-methacryloyloxyethyl acid phosphate (MEP) as an adhesive monomer, 6.5 wt % of hydroxyethyl methacrylate (HEMA) as a hydrophilic monomer, 0.5 wt % of barium glass/silica as an inorganic filler, 20 wt % of acetone as diluent, 5 wt % of water, 0.5 wt % of CQ as a photoinitiator, and 2.5 wt % p-dimethyl aminobenzoate (EDMAB) as a reductant. The physical properties of the prepared adhesive composition measured as described above were shown in Table 3 below.

EXAMPLE 3

The following was mixed to prepare a light-curing dental adhesive composition: 15 wt % of a prepolymer mixture consisting of 60 wt % of Bis-GMA and 40 wt % of Tri-GMA, 8 wt % of 4-methacryloxyethyltrimellitic anhydride (4-META) as an acidic monomer, 35 wt % of 2-methacryloyloxyethyl acid phosphate (MEP) and 10-methacryloyloxydecyl acid phosphate (MDP) (MEP: MDP=50:50) as an adhesive monomer, 7 wt % of HPMA as a hydrophilic monomer, 4 wt % of lithium aluminosilicate as an inorganic filler, 18 wt % of acetone as diluent, 10 wt % of water, 2.5 wt % of CQ as a photoinitiator, and 0.5 wt % of DMAEMA as a reductant. The physical properties of the prepared adhesive composition measured as described above were shown in Table 3 below.

EXAMPLE 4

A light-curing dental adhesive composition was prepared in the same manner as in Example 1, except that 16 wt % of a prepolymer mixture consisting of 50 wt % of Bis-GMA and 50 wt % of Tetra-GMA was used. The physical properties of the prepared adhesive composition measured as described above were shown in Table 3 below.

EXAMPLE 5

A light-curing dental adhesive composition was prepared in the same manner as in Example 2, except that 25 wt % of a prepolymer mixture consisting of 45 wt % of Bis-GMA, 45 wt % of Tri-GMA and 10 wt % of Tetra-GMA was used. The physical properties measured as described above of the prepared adhesive composition were shown in Table 3 below.

COMPARATIVE EXAMPLE 1

A light-curing dental adhesive composition was prepared in the same manner as in Example 2, except that 25 wt % of Bis-GMA was used instead of a prepolymer mixture. The physical properties measured as described above of the prepared adhesive composition were shown in Table 3 below.

COMPARATIVE EXAMPLE 2

A light-curing dental adhesive composition was prepared in the same manner as in Example 1, except that 23 wt % of a prepolymer mixture consisting of 60 wt % of Bis-GMA and 40 wt % of Tri-GMA was used and an acidic monomer was not used. The physical properties of the prepared adhesive composition measured as described above were shown in Table 3 below.

TABLE 3

The results of measured physical properties

| Physical Properties | Examples | | | | | Comparative Examples | |
|---|---|---|---|---|---|---|---|
| | 1 | 2 | 3 | 4 | 5 | 1 | 2 |
| Photoconversion (%) | 54 | 52 | 49 | 45 | 51 | 40 | 42 |
| Polymerization shrinkage (%) | 2.3 | 2.2 | 2.6 | 2.7 | 2.5 | 5.5 | 5.1 |
| Water absorption (%) | 11 | 13 | 12 | 13 | 14 | 26 | 29 |
| Solubility (μg/mm$^3$) | 1.0 | 1.1 | 1.3 | 1.3 | 1.4 | 2.8 | 3.2 |
| Radiopacity | 0.35 | 0.35 | 0.35 | 0.34 | 0.34 | 0.19 | 0.20 |
| Dentine bonding strength (MPa) | 21 | 24 | 22 | 21 | 23 | 11 | 3 |
| Cytotoxicity (RI) | 0/1 | 0/1 | 0/1 | 0/1 | 0/1 | 1/1 | 1/1 |

As shown in above Table 3, the light-curing adhesive compositions comprising the prepolymer mixture of Bis-GMA with Tri-GMA and/or Tetra-GMA prepared in Examples 1 to 5 had better physical and mechanical properties, such as low polymerization shrinkage and water absorption due to hydroxy group blocking, convenience for use by using the reduced amount of diluent due to low viscosity, and superior bonding strength on teeth, compared to the light-curing adhesive composition comprising only the Bis-GMA prepolymer prepared in Comparative Example 1.

Furthermore, the light-curing adhesive composition, which does not comprise acidic monomer, prepared in Comparative Example 2 had poor dentine bonding strength. It is thought to be because the smear layer was not sufficiently removed. Thus, the composition cannot serve as adhesives.

While the present invention has been shown and described with particular examples, it will be apparent to those skilled in the art that many changes and modifications may be made without departing from the spirit and scope of the invention as defined in the appended claims.

What is claimed is:

1. A one-step light-curing dental adhesive composition with improved physical and mechanical properties, and adhesive performance, comprising:
   (a) 1 to 50 wt % of a prepolymer mixture selected from a group consisting of a mixture of 2,2-bis-[4-(2-hydroxy-3-methacryloyloxypropoxy)phenyl]propane (Bis-GMA) of formula 1 with trifunctional methacrylate (Tri-GMA) of formula 2, a mixture of Bis-GMA with tetrafunctional methacrylate (Tetra-GMA) of formula 3 and a mixture of Bis-GMA, Tri-GMA and Tetra-GMA;
   (b) 1 to 30 wt % of an acidic monomer having carboxylic acid or carboxylic anhydride group in a molecule;
   (c) 1 to 40 wt % of an adhesive monomer;
   (d) 1 to 10 wt % of a hydrophilic monomer;
   (e) 0.1 to 5 wt % of an inorganic filler;
   (f) 10 to 60 wt % of diluent;
   (g) 1 to 10 wt % of water; and
   (h) 1 to 10 wt % of a photoinitiation system,
wherein the wt % of all the components are based on the total weight of the composition;

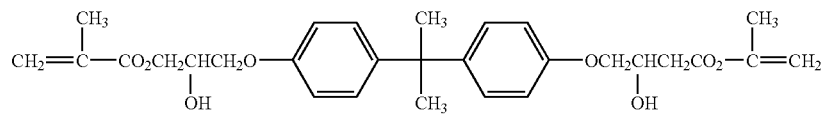
[Formula 1]

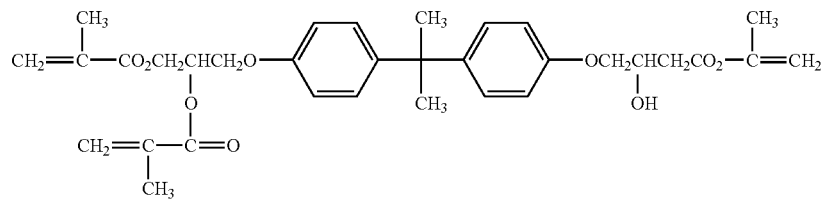
[Formula 2]

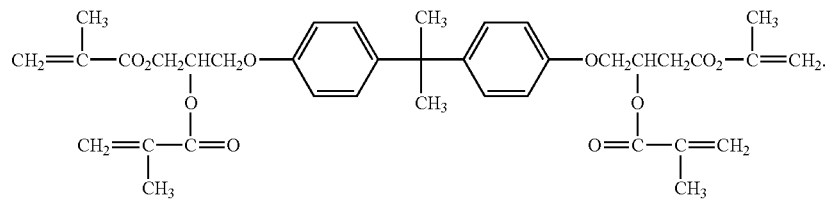
[Formula 3]

2. The one-step light-curing dental adhesive composition according to claim 1, wherein the prepolymer mixture is the mixture of 95 to 5 wt % of Bis-GMA with 5 to 95 wt % of Tri-GMA based on the weight of the prepolymer mixture.

3. The one-step light-curing dental adhesive composition according to claim 1, wherein the prepolymer mixture is the mixture of 95 to 5 wt % of Bis-GMA with 5 to 95 wt % of Tetra-GMA based on the weight of the prepolymer mixture.

4. The one-step light-curing dental adhesive composition according to claim 1, wherein the prepolymer mixture is the mixture of 90 to 5 wt % of Bis-GMA with 90 to 5 wt % of Tri-GMA and 90 to 5 wt % of Tetra-GMA based on the weight of the prepolymer mixture.

5. The one-step light-curing dental adhesive composition according to claim 1, wherein the acid monomer is selected from a group consisting of 4-(meth)acryloxymethyltrimellitic acid and its anhydride, 4-(meth)acryloxyethyltrimellitic acid and its anhydride, 4-(meth)acryloxypropyltrimellitic acid and its anhydride, 4-(meth)acryloxybutyltrimellitic acid and its anhydride, 4-(meth)acryloxypentyltrimellitic acid and its anhydride, 4-(meth)acryloxyhexyltrimellitic acid, 4-(meth)acryloxyoctyltrimellitic acid and its anhydride, and mixtures thereof.

6. The one-step light-curing dental adhesive composition according to claim 1, wherein the adhesive monomer is selected from a group consisting of 2-(meth)acryloyloxyethyl acid phosphate, 2- and 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis[2-(meth)acryloyloxyethyl]acid phosphate, 2-(meth)acryloyloxyethylphenyl acid phosphate, and mixtures thereof.

7. The one-step light-curing dental adhesive composition according to claim 1, wherein the hydrophilic acid is selected from a group consisting of hydroxyethyl methacrylate, hydroxypropyl methacrylate and a mixture thereof.

8. The one-step light-curing dental adhesive composition according to claim 1, wherein the inorganic filler is selected from a group consisting of quartz, barium glass, barium glass/silica, quartz/barium glass, silica, zirconia/silica, aluminosilicate, lithium aluminosilicate and barium aluminosilicate, and mixtures thereof, having a particle diameter of from 0.0005 to 20 μm, of which surface is treated with silane coupling agent.

9. The one-step light-curing dental adhesive composition according to claim 1, wherein the diluent is ethanol or acetone.

10. The one-step light-curing dental adhesive composition according to claim 1, wherein the photoinitiation system comprises 0.05 to 5 wt % of a photoinitiator and 0.05 to 5 wt % of a reductant based on the total weight of the composition.

11. Th one-step light-curing dental adhesive compositions according to claim 10, wherein the photoinitiator is camphorquinone and the reductant is N,N-dimethylaminoethyl methacrylate or ethyl p-dimethyl aminobenzoate.

* * * * *